US012677782B2

(12) United States Patent
Irvine, Jr. et al.

(10) Patent No.: US 12,677,782 B2
(45) Date of Patent: Jul. 14, 2026

(54) BASIL CULTIVAR 'PAS1713599'

(71) Applicant: Ball Horticultural Company, West Chicago, IL (US)

(72) Inventors: James R. Irvine, Jr., Batavia, IL (US); Jhamna Magsig Castillo, San Jose (CR)

(73) Assignee: Ball Horticultural Company, West Chicago, IL (US)

( * ) Notice: Subject to any disclaimer, the term of this patent is extended or adjusted under 35 U.S.C. 154(b) by 219 days.

(21) Appl. No.: 18/601,131

(22) Filed: Mar. 11, 2024

(65) Prior Publication Data

US 2025/0280781 A1    Sep. 11, 2025

(51) Int. Cl.
    *A01H 6/50*        (2018.01)
    *A01H 5/10*        (2018.01)
(52) U.S. Cl.
    CPC .............. *A01H 6/506* (2018.05); *A01H 5/10* (2013.01)
(58) Field of Classification Search
    None
    See application file for complete search history.

(56) References Cited

U.S. PATENT DOCUMENTS

2019/0350152 A1* 11/2019 Kunzemann ............. A01H 5/12
2025/0280780 A1*  9/2025 Irvine, Jr. ............. A01H 6/506

OTHER PUBLICATIONS

U.S. Appl. No. 18/601,128, filed Mar. 11, 2024, James R. Irvine Jr., et al.
Garibaldi, et al., "First Report of Downy Mildew on Basil (*Ocimum basilicum*) in Italy." Plant Disease, 88 (3): 312, (2004).
Mcgrath. "Basil Downy Mildew." Cornell University, Cornell Vegetables. Dated Mar. 2023, Accessed May 6, 2024. Retrieved from <https://www.vegetables.cornell.edu/pest-management/disease-factsheets/basil-downy-mildew/#Symptoms>.
Navet, et al., "Agrobacterium-mediated Transformation of Sweet Basil (*Ocimum basilicum*)." Bio-Protocol 10(22):e3828, (2020).
Roberts, et al., "First Report of Downy Mildew Caused by a *Peronospora* sp. on Basil in Florida and the United States." Plant Disease, 93 (2): 199, (2009).
Simon. "New Crop FactSheet." Purdue University, Center for New Crops & Plants Products, Dated Feb. 23, 1998, Accessed on May 6, 2024. Retrieved from <https://www.hort.purdue.edu/newcrop/CropFactSheets/basil.html>.
Zhang, et al. "Downy Mildew of Basil in South Florida." University of Florida, IFAS Extension, pp. 271, (2019).

* cited by examiner

*Primary Examiner* — Amjad Abraham
*Assistant Examiner* — Brian James Sullivan
(74) *Attorney, Agent, or Firm* — Dentons US LLP

(57)        ABSTRACT

The invention provides plants of the basil cultivar designated 'PAS1713599'. The invention thus relates to the plants, cells, plant parts, and tissue cultures of the cultivar 'PAS1713599', and to methods for producing a basil plant produced by crossing a basil plant of cultivar 'PAS1713599' with another basil plant, such as a plant of another cultivar. The invention further relates to basil seeds and plants produced by crossing plants of cultivar 'PAS1713599' with plants of another cultivar. The invention further relates to the genetic complements and hybrid genetic complements of plants of cultivar 'PAS1713599'.

22 Claims, No Drawings

BASIL CULTIVAR 'PAS1713599'

BACKGROUND OF THE INVENTION

Field of the Invention

The present invention relates to the field of plant breeding and, more specifically, to basil plants having a late flowering trait, an upright habit, small leaves, and downy mildew resistance. In particular, the invention relates to plants of the cultivar designated 'PAS1713599', and derivatives and tissue cultures thereof.

Description of Related Art

Basil, *Ocimum basilicum*, is an important economic and medicinal herb native to tropical regions from Central Africa to Southeast Asia. In temperate climates it is grown as an annual. It is cultivated in regions throughout the United States as a culinary herb, source of essential oil, and a garden ornamental. Cultivars are valued for aroma, leaf size, and plant habit. The delicate aroma of Genovese Dolce Fresca basil makes it a popular culinary herb in particular for use in pesto, the traditional Genovese sauce (New Crop Fact-SHEET, James E. Simon, Purdue University).

In 2003 a significant disease, downy mildew, caused by the Oomycete *Peronospora belbahrii*, was first was observed in several greenhouses located in the Liguria Region of northern Italy where more than 50% of the plants were affected. See Garibaldi, A.; et al. (March 2004). First Report of Downy Mildew on Basil (*Ocimum basilicum*) in Italy. Plant Disease. 88 (3): 312. In the fall of 2007, downy mildew was reported in south Florida from four production locations, and shortly after in west-central north Florida with an incidence of nearly 100% on some of the affected crops and caused complete yield losses on basil grown both in the field for fresh market and potted herbs market. By 2008 it had spread along the eastern United States, reaching Massachusetts. See Roberts, P. D; et al. (February 2009). First Report of Downy Mildew Caused by a *Peronospora* sp. on Basil in Florida and the United States. Plant Disease. 93 (2): 199. It has since been reported in at least 42 states and many other countries.

The most noticeable symptom on affected basil is leaf yellowing like that of a nutrition deficiency, and later a gray, fuzzy growth, downy-appearing sporulation, may be apparent on the underside of the leaf Infected tissue eventually becomes necrotic. While spores are capable of long-distance disease transmission, contaminated seed is likely the mechanism for movement between geographically separated areas. See Zhang, S. et al. (April 2003) Downy Mildew of Basil in South Florida, IFAS Extension PP271.

Downy mildew continues to be the most common and most damaging disease of basil in the United States. Varieties resistant to downy mildew were first marketed in 2018; however, there is a continuing need to develop new downy mildew resistant cultivars to meet market demands. See Cornell University Factsheet (March 2023) Basil Downy Mildew.

SUMMARY OF THE INVENTION

In one aspect, the invention provides a basil plant of cultivar 'PAS1713599'. Also provided are seeds and plants having all of the physiological and morphological characteristics of such plants. Parts of these basil plants are also provided, for example, including a cutting, a stem, a leaf, an axillary bud, a flower, pollen, or an ovule.

In another aspect of the invention, a tissue culture of regenerable cells of basil cultivar 'PAS1713599' is provided. The tissue culture will preferably be capable of regenerating basil plants capable of expressing all of the physiological and morphological characteristics of the starting plant and of regenerating plants having substantially the same genotype as the starting plant. Examples of some of the physiological and morphological characteristics of basil cultivar 'PAS1713599' include those traits set forth in the phenotypic description provided herein. The regenerable cells in such tissue culture may be derived, for example, from a stem, a leaf, an axillary bud, a flower, pollen, or an ovule. Still further, the present invention provides basil plants regenerated from a tissue culture of the invention, the plants having all of the physiological and morphological characteristics of basil cultivar 'PAS1713599'.

In yet another aspect, the invention provides a method of vegetatively propagating a basil plant comprising the steps of: (a) collecting tissue capable of being propagated from a plant of basil cultivar 'PAS1713599'; and (b) propagating a plant from said tissue. The method will preferably be capable of producing basil plants capable of expressing all of the physiological and morphological characteristics of the starting plant and of producing plants having substantially the same genotype as the starting plant. Still further, the present invention provides basil plants produced by vegetative propagation of basil cultivar 'PAS1713599'. In some embodiments, such plants have all of the physiological and morphological characteristics of basil cultivar 'PAS1713599'.

In one aspect, the present invention provides a method of introducing a trait into a basil plant, the method comprising the steps of: (a) utilizing as a recurrent parent a plant of basil cultivar 'PAS1713599' by crossing the plant with a donor basil plant that comprises a trait to produce F1 progeny; (b) selecting an $F_1$ progeny that comprises the trait; (c) backcrossing the selected $F_1$ progeny with a plant of cultivar 'PAS1713599' to produce backcross progeny; and (d) selecting a backcross progeny comprising the trait and the morphological and physiological characteristics of the recurrent parent basil cultivar used in step (a); and (c) repeating steps (c) and (d) three or more times to produce a selected fourth or higher backcross progeny that comprises the trait. In some embodiments, plants produced by such methods are also provided.

In one aspect, a plant of basil cultivar 'PAS1713599' further comprising an added heritable trait is provided. In some embodiments, the heritable trait may comprise a transgene or may comprise a genetic locus that is, for example, a dominant or recessive allele. In specific embodiments, the added genetic locus may confer one or more traits, such as for example, herbicide tolerance, insect resistance, pest resistance, disease resistance, and environmental stress tolerance. In further embodiments, the trait may be conferred by a naturally occurring gene introduced into the genome of a line by backcrossing, a non-transgenic mutation, or a transgene introduced through genetic transformation techniques into the plant or a progenitor of any previous generation thereof. When introduced through transformation, a genetic locus may comprise one or more genes integrated at a single chromosomal location.

In another aspect, a plant of basil cultivar 'PAS1713599' further comprising a single locus conversion is provided. In some embodiments, a single locus conversion includes one or more site-specific changes to the plant genome, such as, without limitation, one or more nucleotide modifications, deletions, or insertions. A single locus may comprise one or more genes or nucleotides integrated or mutated at a single chromosomal location. In one embodiment, a single locus conversion may be introduced by a genetic engineering technique, methods of which include, for example, genome editing with engineered nucleases (GEEN). Engineered nucleases include, but are not limited to, Cas endonucleases; zinc finger nucleases (ZFNs); transcription activator-like effector nucleases (TALENs); engineered meganucleases, also known as homing endonucleases; and other endonucleases for DNA or RNA-guided genome editing that are well-known to the skilled artisan. The single locus conversion may confer one or more traits, such as for example, herbicide tolerance, insect resistance, pest resistance, disease resistance, and environmental stress tolerance.

In yet another aspect, the invention provides a method comprising applying plant breeding techniques to a plant of basil cultivar 'PAS1713599'. In some embodiments, the method comprises producing a basil cultivar 'PAS1713599'-derived basil plant. Non-limiting examples of plant breeding techniques include recurrent selection, mass selection, hybridization, open-pollination, backcrossing, modified backcrossing, pedigree breeding, mutation breeding, or marker assisted selection. In one embodiment, the method comprises selecting a basil cultivar 'PAS1713599'-derived basil plant that comprises the late flowering trait, upright habit, small leaves, or downy mildew resistance found in basil cultivar 'PAS1713599'. In specific embodiments, a basil plant produced by the breeding techniques described herein may have a late flowering trait, an upright habit, small leaves, or downy mildew resistance.

In still yet another aspect, the present invention provides a method of producing a seed of a basil cultivar 'PAS1713599'-derived basil plant, the method comprising the steps of: (a) producing a basil cultivar 'PAS1713599'-derived basil plant from a seed produced by crossing a plant of basil cultivar 'PAS1713599' with itself or a second basil plant; and (b) crossing the basil cultivar 'PAS1713599'-derived basil plant with itself or a different basil plant to obtain a seed of a further basil cultivar 'PAS1713599'-derived basil plant. In some embodiments, the method further comprises repeating the producing and crossing steps of (a) and (b) using the seed from step (b) for producing a plant according to step (a) for at least one generation to produce a seed of an additional basil cultivar 'PAS1713599'-derived basil plant.

Any embodiment discussed herein with respect to one aspect of the invention applies to other aspects of the invention as well, unless specifically noted.

The term "about" is used to indicate that a value includes the standard deviation of the mean for the device or method being employed to determine the value. The use of the term "or" in the claims is used to mean "and/or" unless explicitly indicated to refer to alternatives only or the alternatives are mutually exclusive. When used in conjunction with the word "comprising" or other open language in the claims, the words "a" and "an" denote "one or more," unless specifically noted otherwise. The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps. Similarly, any plant that "comprises,"

"has" or "includes" one or more traits is not limited to possessing only those one or more traits and covers other unlisted traits.

Other objects, features, and advantages of the present invention will become apparent from the following detailed description. It should be understood, however, that the detailed description and any specific examples provided, while indicating specific embodiments of the invention, are given by way of illustration only, since various changes and modifications within the spirit and scope of the invention will become apparent to those skilled in the art from this detailed description.

DETAILED DESCRIPTION OF THE INVENTION

Definitions

Allele: Any of one or more alternative forms of a gene locus, all of which alleles relate to one trait or characteristic. In a diploid cell or organism, the two alleles of a given gene occupy corresponding loci on a pair of homologous chromosomes.

Backcrossing: A process in which a breeder repeatedly crosses hybrid progeny back to one of the parents, for example, a first generation hybrid $(F_1)$ with one of the parental genotypes of the $F_1$ hybrid.

Crossing: The pollination of a female flower of a basil plant, thereby resulting in the production of seed from the flower.

Cross-pollination: Fertilization by the union of two gametes from different plants.

Diploid: A cell or organism having two sets of chromosomes.

Tetraploid: A cell or organism having four sets of chromosomes.

$F_1$ Hybrid: The first generation progeny of the cross of two plants.

Genetic Complement: An aggregate of nucleotide sequences, the expression of which sequences defines the phenotype in basil plants, or components of plants including cells or tissue.

Genotype: The genetic constitution of a cell or organism.

Haploid: A cell or organism having one set of the two sets of chromosomes in a diploid.

Linkage: A phenomenon wherein alleles on the same chromosome tend to segregate together more often than expected by chance if their transmission was independent.

Marker: A readily detectable phenotype, preferably inherited in codominant fashion (both alleles at a locus in a diploid heterozygote are readily detectable), with no environmental variance component, i.e., heritability of 1.

Non-transgenic mutation: A mutation that is naturally occurring (spontaneous) or induced by conventional methods (e.g. exposure of plants to radiation or mutagenic compounds), not including mutations made using recombinant DNA techniques.

Phenotype: The detectable characteristics of a cell or organism in which the characteristics are the manifestation of gene expression.

Quantitative Trait Loci (QTL): Genetic loci that contribute, at least in part, certain numerically representable traits that are usually continuously distributed.

Regeneration: The development of a plant from tissue culture.

SSR profile: A profile of simple sequence repeats used as genetic markers and scored by gel electrophoresis following PCR amplification using flanking oligonucleotide primers.

Self-pollination: The transfer of pollen from the anther to the stigma of the same plant.

Single Locus Converted (Conversion) Plant: Plants that are developed by a plant breeding technique called back-crossing or by genetic engineering of a locus, wherein essentially all of the morphological and physiological characteristics of a plant are recovered in addition to the characteristics conferred by the single locus transferred into the plant via the backcrossing or genetic engineering technique.

Substantially Equivalent: A characteristic that, when compared, does not show a statistically significant difference (e.g., p=0.05) from the mean.

Tissue Culture: A composition comprising isolated cells of the same or a different type or a collection of such cells organized into parts of a plant.

Transgene: A genetic sequence that has been introduced into the nuclear or chloroplast genome of a basil plant by genetic transformation or site-specific modification.

The following examples are included to demonstrate preferred embodiments of the invention. It should be appreciated by those of skill in the art that the techniques disclosed in the examples that follow represent techniques discovered by the inventor to function well in the practice of the invention, and thus can be considered to constitute preferred modes for its practice. However, those of skill in the art should, in light of the present disclosure, appreciate that many changes can be made in the specific embodiments that are disclosed and still obtain a like or similar result without departing from the spirit and scope of the invention.

*Ocimum basilicum* Cultivar 'Pas1713599'

Provided herein are methods and compositions relating to plants, seeds, and derivatives of basil cultivar 'PAS1713599'. This cultivar shows uniformity and stability within the limits of environmental influence for the traits described hereinafter. In particular, basil cultivar 'PAS1713599' exhibits late flowering, an upright habit, small leaves, and significant downy mildew resistance.

A. Origin and Breeding History

Basil cultivar 'PAS1713599' was developed using a pedigree breeding system. The original developmental cross was made in a greenhouse in Elburn, Illinois in 2018 using the proprietary inbred line coded DR4 as the female parent, and the proprietary inbred line coded EE29 as the male parent. The resulting F1 progeny seed from this cross was sown in a greenhouse, in Cartago, Costa Rica, and from this population single plant selections were made and selfed.

In 2019, the F2 progeny plants were evaluated for several agronomic selection criteria, including late flowering, small leaves, and disease resistance. Resistance to downy mildew was confirmed through natural infection relative to susceptible controls. Single plant selections were made and selfed, and in 2020 F3 progeny plants were selected based on uniformity for the stated selection criteria. Single plant selections were made and selfed to produce F4 progeny that were advanced through single plant selection and selfing.

During 2021 the F4 progeny were evaluated and advanced through single plant selection and selfing to yield F5 progeny. One F5 family coded AA3913E was massed in 2022 to produce breeder seed. In 2023 the mass seed from 2022 was used to make stock seed. The plants massed in 2022 and 2023 were uniform and stable. No variants or off types were observed in either the breeders seed increase or the stock seed increase. Line AA3913E was later designated as cultivar 'PAS1713599'. It was stable and uniform after two generations of seed increase, which includes the breeders seed increase and the stock seed increase.

B. Phenotypic Description

In accordance with another aspect of the present invention, there is provided a basil plant having the morphological characteristics of basil cultivar 'PAS1713599'. A description of the morphological and physiological characteristics of basil plant 'PAS1713599' is presented in Table 1.

The following characteristics have been repeatedly observed and can be used to distinguish 'PAS1713599' as a new and distinct cultivar of *Ocimum basilicum* plant:

1. Late flowering;
2. Upright growth habit;
3. Small leaves; and
4. Significant Downy Mildew resistance.

'PAS1713599' has not been observed under all possible environmental conditions. Phenotype may vary due to environmental influence without variation in genotype. Basil cultivar 'PAS1713599' shows uniformity and stability within the limits of environmental influence for the traits described herein. No variant traits have been observed or are expected in 'PAS1713599'.

TABLE 1

Morphological Characteristics of Cultivar 'PAS1713599'

| CHARACTERISTIC | |
| --- | --- |
| 1. PLANT: | |
| Plant Growth Habit | Upright |
| Plant Height at Maturity | Medium 57.6 cm |
| 2. STEM: | |
| Stem Anthocyanin Coloration: | Absent |
| 3. LEAF BLADE: | |
| Leaf Blade Shape | Broad Ovate |
| Leaf Blade Length | Short 5.9 cm |
| Leaf Blade Width | Medium 3.6 cm |
| Leaf Blade Intensity of Anthocyanin Coloration | Absent |
| Leaf Blade Intensity of Green Color | Medium |
| Leaf Blade Glossiness | Medium |
| Leaf Blade Blistering | Medium |
| Leaf Blade Profile in Cross Section | Convex |
| Leaf Blade Serration of Margin | Weak |
| Leaf Blade Undulation of Margin | Absent or Very Weak |
| 4. PETIOLE: | |
| Petiole Length | Short 1.2 cm |
| 5. FLOWERING STEM: | |
| Flowering Stem Length | Medium 10.5 cm |
| Flowering Stem Length of Internodes | Short 2.2 cm |
| Flowering Stem Pubescence of Upper Sepal | Weak |
| 6. FLOWER: | |
| Flower Color of Corolla | White |
| Flower Color of Style | White |
| Flower Timing | Late |
| Days to Flower Induction (From Sowing) | 86 |
| Days to Full Flower (From Sowing) | 88 |

* These are typical values. Values may vary due to environment. Other values that are substantially equivalent are also within the scope of the invention.

C. Deposit Information

A deposit of representative sample of seed of basil cultivar 'PAS1713599' was made with the Provasoli-Guillard National Center for Marine Algae and Microbiota (NCMA), 60 Bigelow Drive, East Boothbay, Maine, 04544 USA. The deposit was assigned NCMA Accession No. 20602003. The date of deposit of the representative sample of plant seed with the NCMA was Feb. 13, 2026. The deposit has been accepted under the Budapest Treaty and will be maintained in the NCMA depository for a period of 30 years, or 5 years after the most recent request, or for the enforceable life of the patent, whichever is longer, and will be replaced if necessary, during that period. Upon issuance, all restrictions on the availability to the public of the deposit will be irrevocably removed consistent with all of the requirements of the Budapest Treaty and 37 C.F.R. §§ 1.801-1.809. Applicant does not waive any infringement of rights granted under this patent or under the Plant Variety Protection Act (7 USC 2321 et seq.).

Further Embodiments of the Invention

A. Plant Breeding

In one aspect, the present disclosure provides plants modified using the methods described herein to include at least a first desired heritable trait. Such plants may, in one embodiment, be developed by backcrossing, wherein essentially all of the desired morphological and physiological characteristics of a cultivar are recovered in addition to a genetic locus transferred into the plant via the backcrossing technique. The term single locus converted plant as used herein refers to those plants which are developed by backcrossing or by genetic engineering, wherein essentially all of the desired morphological and physiological characteristics of a cultivar are recovered in addition to the single locus transferred into the cultivar via the backcrossing or genetic engineering technique, respectively. By essentially all of the desired morphological and physiological characteristics, it is meant that the characteristics of a plant are recovered that are otherwise present when compared in the same environment, other than an occasional variant trait that might arise during backcrossing, direct introduction of a transgene, or application of genetic engineering technique.

Backcrossing methods can be used with the present invention to improve or introduce a trait into a cultivar. The term backcrossing as used herein refers to the repeated crossing of a hybrid progeny back to one of the parental basil plants. The parental basil plant that contributes the locus or loci for the desired trait is termed the nonrecurrent or donor parent. This terminology refers to the fact that the nonre-current parent is used one time in the backcross protocol and therefore does not recur. The recurrent parent therefore provides the desired genetic background, while the choice of the particular nonrecurrent parent will depend on the pur-pose of the backcross. One of the major purposes is to add some commercially desirable trait to the plant. The exact backcrossing protocol will depend on the characteristic or trait being altered and the genetic distance between the recurrent and nonrecurrent parents. Although backcrossing methods are simplified when the characteristic being trans-ferred is a dominant allele, a recessive allele, or an additive allele (between recessive and dominant) may also be trans-ferred. In this instance it may be necessary to introduce a test of the progeny to determine if the desired characteristic has been successfully transferred. The backcross process may be accelerated by the use of genetic markers, such as SSR, RFLP, SNP or AFLP markers to identify plants with the greatest genetic complement from the recurrent parent.

Modified backcrossing may also be used with the plants provided herein. This technique uses different recurrent parents during the backcrossing. Modified backcrossing may be used to replace the original recurrent parent with a variety having certain more desirable characteristics or multiple parents may be used to obtain different desirable character-istics from each.

With the development of molecular markers associated with particular traits, it is possible to add additional traits into an established germ line, such as represented here, with the end result being substantially the same base germplasm with the addition of a new trait or traits. Molecular breeding, as described in Moose and Mumm, 2008 (*Plant Physiol.,* 147:969-977), for example, and elsewhere, provides a mechanism for integrating single or multiple traits or QTL into an elite line. This molecular breeding-facilitated move-ment of a trait or traits into an elite line may encompass incorporation of a particular genomic fragment associated with a particular trait of interest into the elite line by the mechanism of identification of the integrated genomic frag-ment with the use of flanking or associated marker assays. In the embodiment represented here, one, two, three or four genomic loci, for example, may be integrated into an elite line via this methodology. When this elite line containing the additional loci is further crossed with another parental elite line to produce hybrid offspring, it is possible to then incorporate at least eight separate additional loci into the hybrid. In one embodiment, each locus may confer a sepa-rate trait. In another embodiment, loci may need to be homozygous and exist in each parent line to confer a trait in the hybrid. In yet another embodiment, multiple loci may be combined to confer a single robust phenotype of a desired trait.

Many traits have been identified that are not regularly selected for in the development of a new variety but that can be improved by backcrossing techniques. A genetic locus conferring the traits may or may not be transgenic. Examples of such traits known to those of skill in the art include, but are not limited to, herbicide tolerance, disease resistance, and pest resistance. These genes are generally inherited through the nucleus, but may be inherited through the cytoplasm.

Selection of basil plants for breeding is not necessarily dependent on the phenotype of a plant and instead can be based on genetic investigations. For example, one can utilize a suitable genetic marker which is closely genetically linked to a trait of interest. One of these markers can be used to identify the presence or absence of a trait in the offspring of a particular cross and can be used in selection of progeny for continued breeding. This technique is commonly referred to as marker assisted selection. Any other type of genetic marker or other assay which is able to identify the relative presence or absence of a trait of interest in a plant can also be useful for breeding purposes. Procedures for marker assisted selection are well known in the art. Such methods will be of particular utility in the case of recessive traits and variable phenotypes, or where conventional assays may be more expensive, time consuming, or otherwise disadvanta-geous. In addition, marker assisted selection may be used to identify plants comprising desirable genotypes at the seed, seedling, or plant stage, to identify or assess the purity of a cultivar, to catalog the genetic diversity of a germplasm collection, and to monitor specific alleles or haplotypes within an established cultivar.

Types of genetic markers which could be used in accor-dance with the invention include, but are not necessarily limited to, Simple Sequence Length Polymorphisms (SSLPs) (Williams et al., *Nucleic Acids Res.,* 1 8:6531-6535, 1990), Randomly Amplified Polymorphic DNAs (RAPDs), DNA Amplification Fingerprinting (DAF), Sequence Char-acterized Amplified Regions (SCARs), Arbitrary Primed Polymerase Chain Reaction (AP-PCR), Amplified Fragment Length Polymorphisms (AFLPs) (EP 534 858, specifically incorporated herein by reference in its entirety), and Single Nucleotide Polymorphisms (SNPs) (Wang et al., *Science*, 280:1077-1082, 1998).

In particular embodiments of the invention, marker assisted selection is used to increase the efficiency of a backcrossing breeding scheme for producing a basil line comprising a desired trait. This technique is commonly referred to as marker assisted backcrossing (MABC). This technique is well-known in the art and may involve, for example, the use of three or more levels of selection, including foreground selection to identity the presence of a desired locus, which may complement or replace phenotype screening protocols; recombinant selection to minimize linkage drag; and background selection to maximize recurrent parent genome recovery.

B. Breeding of Basil Cultivar 'PAS1713599'

The development of new varieties using one or more starting varieties is well known in the art and encompassed by the disclosure. In accordance with the disclosure, novel varieties may be created by crossing a plant of the disclosure followed by multiple generations of breeding according to such well-known methods. New varieties may be created by crossing with any second plant. New varieties may be developed, for example, by applying a breeding technique to a plant of basil cultivar 'PAS1713599'. Such breeding techniques are well-known in the art and include but are not limited to recurrent selection, mass selection, hybridization, open-pollination, backcrossing, modified backcrossing, pedigree breeding, mutation breeding, and marker assisted selection. "Mutation breeding" as used herein refers to a breeding technique comprising selecting a naturally occurring (spontaneous) mutation or inducing a mutation through means such as irradiation or chemical induction.

In selecting a second plant to cross with a plant of the disclosure, it will typically be preferred to choose those plants which either themselves exhibit one or more selected desirable characteristics or which exhibit the desired characteristic(s) when in hybrid combination. Once initial crosses have been made, selection takes place to produce new varieties. Examples of desirable traits may include, in specific embodiments, late flowering, upright growth habit, foliage quality, shape and uniformity, small leaves, seed germination rate, seedling vigor, pest and disease resistance, herbicide tolerance, and adaptability for soil and climate conditions. Consumer-driven traits are other traits that may be incorporated into new plants developed by this disclosure.

One aspect of the current disclosure therefore provides methods for producing a basil plant comprising a desirable trait, e.g. a late flowering trait, an upright habit, small leaves, or downy mildew resistance, found in basil plant of cultivar 'PAS1713599'. In certain embodiments, the method may comprise (a) producing an basil cultivar 'PAS1713599'-derived basil plant from a seed produced by crossing a plant of basil cultivar 'PAS1713599' with itself or a second basil plant; (b) crossing the basil cultivar 'PAS1713599'-derived basil plant with itself or a different basil plant to obtain a seed of a further basil cultivar 'PAS1713599'-derived basil plant; (c) selecting a further basil cultivar 'PAS1713599'-derived basil plant that comprises the desirable trait; (d) repeating said producing, crossing, and selecting steps of (a), (b), and (c) using the seed of said step (b) for at least one generation to produce a seed an additional 'PAS1713599'-derived basil plant; and (c) selecting an additional basil cultivar 'PAS1713599'-derived basil plant that comprising the desirable trait. In a particular embodiment, the second plant may be a basil plant and the progeny seed may be planted and grown to produce fertile hybrid progeny plants. A plant in accordance with the disclosure may be used in such crosses as the female plant or the male plant.

The disclosure also provides methods of producing basil plants derived from basil cultivar 'PAS1713599'. The method may comprise (a) crossing a basil plant of basil cultivar 'PAS1713599' with itself or a second plant capable of being crossed thereto; and (b) collecting resulting seed. In one embodiment, the second plant may be a basil plant. In some embodiments, the methods of the present disclosure may further comprise the step of (c) crossing a plant grown from said seed of step (b) with itself or a second plant at least one or more additional time(s) to yield additional seed. Plants, seeds, and plant parts produced from the methods described herein are also provided.

In certain embodiments, hybrid seeds may be produced using the methods of the present disclosure. A parent plant of such a seed may be a basil plant of basil cultivar 'PAS1713599'. In other embodiments, a plant as described herein may be either the male plant or the female plant in a given cross.

In accordance with the disclosure, any species of basil may be used. In particular, *Ocimum* species that may be useful include but are not limited to *Ocimum basilicum, Ocimum americanum, Ocimum kilimandscharicum*, and the like.

C. Plants Derived by Genetic Engineering

Various genetic engineering technologies have been developed and may be used by those of skill in the art to introduce traits in plants. In certain aspects of the claimed invention, traits are introduced into basil plants via altering or introducing a single genetic locus or transgene into the genome of a recited variety or progenitor thereof. Methods of genetic engineering to modify, delete, or insert genes and polynucleotides into the genomic DNA of plants are well-known in the art.

In specific embodiments of the invention, improved basil cultivars can be created through the site-specific modification of a plant genome. Methods of genetic engineering include, for example, utilizing sequence-specific nucleases such as zinc-finger nucleases (see, for example, U.S. Pat. Appl. Pub. No. 2011-0203012); engineered or native meganucleases; TALE-endonucleases (see, for example, U.S. Pat. Nos. 8,586,363 and 9,181,535); and RNA-guided endonucleases, such as those of the CRISPR/Cas systems (see, for example, U.S. Pat. Nos. 8,697,359 and 8,771,945 and U.S. Pat. Appl. Pub. No. 2014-0068797). One embodiment of the invention thus relates to utilizing a nuclease or any associated protein to carry out genome modification. This nuclease could be provided heterologously within donor template DNA for templated-genomic editing or in a separate molecule or vector. A recombinant DNA construct may also comprise a sequence encoding one or more guide RNAs to direct the nuclease to the site within the plant genome to be modified. Further methods for altering or introducing a single genetic locus include, for example, utilizing single-stranded oligonucleotides to introduce base pair modifications in a basil plant genome (see, for example Sauer et al., *Plant Physiol*, 170 (4): 1917-1928, 2016).

Methods for site-directed alteration or introduction of a single genetic locus are well-known in the art and include those that utilize sequence-specific nucleases, such as the aforementioned, or complexes of proteins and guide-RNA that cut genomic DNA to produce a double-strand break (DSB) or nick at a genetic locus. As is well-understood in the art, during the process of repairing the DSB or nick introduced by the nuclease enzyme, a donor template, transgene, or expression cassette polynucleotide may become integrated into the genome at the site of the DSB or nick. The presence of homology arms in the DNA to be integrated may promote the adoption and targeting of the insertion sequence into the plant genome during the repair process through homologous recombination or non-homologous end joining (NHEJ).

In another embodiment of the invention, genetic transformation may be used to insert a selected transgene into a plant of the disclosure or may, alternatively, be used for the preparation of transgenes which can be introduced by backcrossing. Methods for the transformation of plants that are well known to those of skill in the art and applicable to many plant species include, but are not limited to, electroporation, microprojectile bombardment, Agrobacterium-mediated transformation, and direct DNA uptake by protoplasts. For example, Navet, et al., describes Agrobacterium-mediated transformation of Ocimum basilicum (Bio Protoc. 2020 Nov. 20; 10(22):e3828).

To effect transformation by electroporation, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wound tissues in a controlled manner.

An efficient method for delivering transforming DNA segments to plant cells is microprojectile bombardment. In this method, particles are coated with nucleic acids and delivered into cells by a propelling force. Exemplary particles include those comprised of tungsten, platinum, and preferably, gold. For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate.

An illustrative embodiment of a method for delivering DNA into plant cells by acceleration is the Biolistics Particle Delivery System, which can be used to propel particles coated with DNA or cells through a screen, such as a stainless steel or Nytex screen, onto a surface covered with target cells. The screen disperses the particles so that they are not delivered to the recipient cells in large aggregates. It is believed that a screen intervening between the projectile apparatus and the cells to be bombarded reduces the size of projectiles aggregate and may contribute to a higher frequency of transformation by reducing the damage inflicted on the recipient cells by projectiles that are too large. Microprojectile bombardment techniques are widely applicable and may be used to transform virtually any plant species.

Agrobacterium-mediated transfer is another widely applicable system for introducing gene loci into plant cells. An advantage of the technique is that DNA can be introduced into whole plant tissues, thereby bypassing the need for regeneration of an intact plant from a protoplast. Modern Agrobacterium transformation vectors are capable of replication in E. coli as well as Agrobacterium, allowing for convenient manipulations. Moreover, recent technological advances in vectors for Agrobacterium-mediated gene transfer have improved the arrangement of genes and restriction sites in the vectors to facilitate the construction of vectors capable of expressing various polypeptide coding genes.

The vectors described have convenient multi-linker regions flanked by a promoter and a polyadenylation site for direct expression of inserted polypeptide coding genes. Additionally, Agrobacterium containing both armed and disarmed Ti genes can be used for transformation.

In those plant strains where Agrobacterium-mediated transformation is efficient, it is the method of choice because of the facile and defined nature of the gene locus transfer. The use of Agrobacterium-mediated plant integrating vectors to introduce DNA into plant cells is well known in the art (U.S. Pat. No. 5,563,055, incorporated herein by reference in its entirety). Transformation of plant protoplasts also can be achieved using methods based on calcium phosphate precipitation, polyethylene glycol treatment, electroporation, and combinations of these treatments.

A number of promoters have utility for plant gene expression for any gene of interest including but not limited to selectable markers, scoreable markers, genes for pest and disease resistance, and any other gene of agronomic interest. Examples of constitutive promoters useful for driving gene expression in plants include, but are not limited to, the cauliflower mosaic virus (CaMV) P-35S promoter, which confers constitutive, high-level expression in most plant tissues, including monocots; a tandemly duplicated version of the CaMV 35S promoter, the enhanced 35S promoter (P-e35S) the nopaline synthase promoter, the octopine synthase promoter; and the figwort mosaic virus (P-FMV) promoter as described in U.S. Pat. No. 5,378,619 (incorporated herein by reference in its entirety), and an enhanced version of the FMV promoter (P-eFMV) where the promoter sequence of P-FMV is duplicated in tandem, the cauliflower mosaic virus 19S promoter, a sugarcane bacilliform virus promoter, a commelina yellow mottle virus promoter, and other plant DNA virus promoters known to express in plant cells.

A variety of plant gene promoters that are regulated in response to environmental, hormonal, chemical, and/or developmental signals can be used for expression of an operably linked gene in plant cells, including promoters regulated by (1) heat, (2) light (e.g., pea rbcS-3A promoter; maize rbcS promoter; or chlorophyll a/b-binding protein promoter), (3) hormones, such as abscisic acid, (4) wounding (e.g., wunl); or (5) chemicals such as methyl jasmonate, salicylic acid, or Safener. It may also be advantageous to employ organ-specific promoters.

Exemplary nucleic acids which may be introduced to the plants of this disclosure include, for example, DNA sequences or genes from another species, or even genes or sequences which originate with or are present in the same species, but are incorporated into recipient cells by genetic engineering methods rather than classical reproduction or breeding techniques. However, the term "exogenous" is also intended to refer to genes that are not normally present in the cell being transformed, or perhaps simply not present in the form, structure, etc., as found in the transforming DNA segment or gene, or genes which are normally present and that one desires to express in a manner that differs from the natural expression pattern, e.g., to over-express. Thus, the term "exogenous" gene or DNA is intended to refer to any gene or DNA segment that is introduced into a recipient cell, regardless of whether a similar gene may already be present in such a cell. The type of DNA included in the exogenous DNA can include DNA, which is already present in the plant cell, DNA from another plant, DNA from a different organism, or a DNA generated externally, such as a DNA sequence containing an antisense message of a gene, or a DNA sequence encoding a synthetic or modified version of a gene.

Many hundreds if not thousands of different genes are known and could potentially be introduced into a plant of basil cultivar 'PAS1713599'. Non-limiting examples of particular genes and corresponding phenotypes one may choose to introduce into a of the disclosure include one or more genes for insect tolerance, such as a *Bacillus thuringiensis* (B.t.) gene, pest tolerance such as genes for fungal disease control, herbicide tolerance such as genes conferring glyphosate tolerance, and genes for quality improvements such as environmental or stress tolerances, or any desirable changes in plant physiology, growth, development, morphology or plant product(s). For example, structural genes would include any gene that confers insect tolerance including but not limited to a *Bacillus* insect control protein gene as described in WO 99/31248, U.S. Pat. Nos. 5,689,052, 5,500,365, and 5,880,275, each of which are herein incorporated by reference in their entirety. In another embodiment, the structural gene can confer tolerance to the herbicide glyphosate as conferred by genes including, but not limited to *Agrobacterium* strain CP4 glyphosate resistant EPSPS gene (aroA:CP4) as described in U.S. Pat. No. 5,633,435, herein incorporated by reference in its entirety, or glyphosate oxidoreductase gene (GOX) as described in U.S. Pat. No. 5,463,175, herein incorporated by reference in its entirety.

Alternatively, the DNA coding sequences can affect these phenotypes by encoding a non-translatable RNA molecule that causes the targeted inhibition of expression of an endogenous gene, for example via antisense- or co-suppression-mediated mechanisms. The RNA could also be a catalytic RNA molecule (i.e., a ribozyme) engineered to cleave a desired endogenous mRNA product. Thus, any gene which produces a protein or mRNA which expresses a phenotype or morphology change of interest is useful for the practice of the present disclosure.

D. Genetic Complements

In another aspect of the invention, the genetic complement of the basil plant cultivar designated 'PAS1713599' is provided. The phrase "genetic complement" is used to refer to the aggregate of nucleotide sequences, the expression of which sequences defines the phenotype of, in the present case, a basil plant, or a cell or tissue of that plant. A genetic complement thus represents the genetic makeup of cell, tissue or plant, and a hybrid genetic complement represents the genetic makeup of a hybrid cell, tissue, or plant. The invention thus provides basil plant cells that have a genetic complement in accordance with the basil plant cells disclosed herein, and plants, seeds and diploid plants containing such cells.

Plant genetic complements may be assessed by genetic marker profiles, and by the expression of phenotypic traits that are characteristic of the expression of the genetic complement, e.g., isozyme typing profiles. It is understood that cultivar 'PAS1713599' could be identified by any of the many well-known techniques such as, for example, Simple Sequence Length Polymorphisms (SSLPs) (Williams et al., *Nucleic Acids Res.,* 18:6531-6535, 1990), Randomly Amplified Polymorphic DNAs (RAPDs), DNA Amplification Fingerprinting (DAF), Sequence Characterized Amplified Regions (SCARs), Arbitrary Primed Polymerase Chain Reaction (AP-PCR), Amplified Fragment Length Polymorphisms (AFLPs) (EP 534 858, specifically incorporated herein by reference in its entirety), and Single Nucleotide Polymorphisms (SNPs) (Wang et al., *Science,* 280:1077-1082, 1998).

In yet another aspect, the present invention provides hybrid genetic complements, as represented by basil plant cells, tissues, plants, and seeds, formed by the combination of a haploid genetic complement of a basil plant of the invention with a haploid genetic complement of the same or a different cultivar. In another aspect, the present invention provides a basil plant regenerated from a tissue culture that comprises a hybrid genetic complement of this invention.

E. Additional Traits

Additional traits can be introduced into the basil cultivar of the present invention. A non-limiting example of such a trait is a coding sequence that decreases RNA and/or protein levels. The decreased RNA and/or protein levels may be achieved through RNAi methods, such as those described in U.S. Pat. No. 6,506,559 to Fire and Mellow.

Another trait that may find use with the basil cultivar of the invention is a sequence that allows for site-specific recombination. Examples of such sequences include the FRT sequence, used with the FLP recombinase (Zhu and Sadowski, *J. Biol. Chem.,* 270:23044-23054, 1995); and the LOX sequence, used with CRE recombinase (Sauer, *Mol. Cell. Biol.,* 7:2087-2096, 1987). The recombinase genes can be encoded at any location within the genome of the basil plant and are active in the hemizygous state.

It may also be desirable to make basil plants more tolerant to or more easily transformed with *Agrobacterium tumefaciens.* Expression of p53 and iap, two baculovirus cell-death suppressor genes, inhibited tissue necrosis and DNA cleavage. Additional targets can include plant-encoded proteins that interact with the *Agrobacterium* Vir genes; enzymes involved in plant cell wall formation; and histones, histone acetyltransferases and histone deacetylases (reviewed in Gelvin, *Microbiology & Mol. Biol. Reviews,* 67:16-37, 2003).

F. Plants Comprising Non-Transgenic Mutations

In still yet another aspect, a plant of basil cultivar designated 'PAS1713599', further comprising a non-transgenic mutation is provided. The phrase "non-transgenic mutation" is used herein to refer to a mutation that is naturally occurring (spontaneous), or induced by conventional methods (e.g. exposure of plants to radiation or mutagenic compounds), not including mutations made using recombinant DNA techniques. Various mutagenesis techniques have been developed and may be used by those of skill in the art to induce mutations in plants. Methods of mutagenesis may include, for example, exposure to irradiation, mutagenic compounds, extreme heat, or tissue culture conditions; long-term seed storage; and targeting induced local lesions in genomes (TILLING). In some embodiments, ionizing radiation may be produced by X-rays, gamma rays, neutrons, beta rays, or ultraviolet rays. Non-limiting examples of chemical mutagens include base analogues, antibiotics, alkylating agents, sodium azide, hydroxylamine, nitrous acid, methylnitrilsourea, and acridines. Methods of mutagenesis to modify, delete, or insert polynucleotides into the genomic DNA are well-known in the art.

In one aspect, improved basil cultivars may be created through mutation of the plant genome. In one embodiment, a plant of the basil cultivar 'PAS1713599' may be subjected to a mutagenesis technique to create a population of mutant plants. Such mutant plants, for example, may comprise a mutation and otherwise comprise all of the physiological and morphological characteristics of basil cultivar 'PAS1713599'. In particular embodiments, mutant plants may comprise a mutation and otherwise comprise all of the morphological and physiological characteristics of basil cultivar 'PAS1713599'.

G. Tissue Cultures and In Vitro Regeneration of Basil Plants

In another aspect, the invention relates to tissue cultures of the basil plant designated 'PAS1713599'. As used herein, the term "tissue culture" indicates a composition comprising isolated cells of the same or a different type or a collection of such cells organized into parts of a plant. Exemplary types of tissue cultures are protoplasts, calli and plant cells that are intact in plants or parts of plants, such as embryos, meristems, cotyledons, pollen, leaves, anthers, roots, root tips, pistil, flower, seed, stems, and the like. In a preferred embodiment, the tissue culture comprises cells derived from immature tissues of these plant parts. Means for preparing and maintaining plant tissue cultures are well known in the art (Abbasi, et al., *In Vitro Cell Dev. Biol.—Plant,* 43:481-492, 2007, and Parsons, et al., *Pharm. Biol.,* 56 (1): 485-494, 2018, each incorporated herein by reference in their entirety).

In yet another aspect, compositions are provided comprising a cell of basil cultivar 'PAS1713599' comprised in plant cell growth media. Plant cell growth media are well known to those of skill in the art. For example, Trettel, et al., describes In vitro organogenesis and growth of *Ocimum basilicum* 'Genovese' (basil) cultivated with growth regulators. (Australian Journal of Crop Science, 2019; specifically incorporated herein by reference). Plant cell growth media can provide adequate support for plant cells, including providing moisture and/or nutritional components.

H. Processes of Crossing Basil Plants and the Basil Plants Produced by Such Crosses The present invention provides processes of preparing novel basil plants and basil plants produced by such processes. In accordance with such a process, a first parent basil plant may be crossed with a second parent basil plant wherein at least one of the first and second basil plants is the basil plant 'PAS1713599'. One application of the process is in the production of $F_1$ hybrid plants. Another important aspect of this process is that it can be used for the development of novel cultivars. For example, the basil plant 'PAS1713599' could be crossed to any second plant, and the resulting hybrid progeny could be vegetatively propagated, or the hybrid progeny could be each selfed for about 5 to 7 or more generations, thereby providing a large number of distinct cultivars. These cultivars could then be crossed with other cultivars and the resulting hybrid progeny analyzed for beneficial characteristics. In this way, novel cultivars conferring desirable characteristics could be identified. "Vegetative propagation" as used herein refers to any form of asexual reproduction occurring in plants in which a new plant grows from a fragment of the parent plant. Non-limiting examples of vegetative propagation methods include tissue culture and division.

I. $F_1$ Hybrid Basil Plant and Seed Production

One beneficial use of the instant basil cultivar is in the production of hybrid seed. Any time the basil plant 'PAS1713599' is crossed with another, different, basil plant, a first generation ($F_1$) basil hybrid plant is produced. As such, an $F_1$ hybrid basil plant can be produced by crossing 'PAS1713599' with any second basil plant. Essentially any other basil plant can be used to produce a hybrid basil plant having basil plant 'PAS1713599' as one parent. All that is required is that the second plant be fertile, which basil plants naturally are, and that the plant is not basil cultivar 'PAS1713599'.

The goal of the process of producing an $F_1$ hybrid is to manipulate the genetic complement of basil to generate new combinations of genes that interact to yield new or improved traits (phenotypic characteristics). If the alleles are the same at a locus, there is said to be homozygosity. If they are different, there is said to be heterozygosity. Hundreds of basil varieties are known to those of skill in the art, any one of which could be crossed with basil plant 'PAS1713599' to produce a hybrid plant.

When the basil plant 'PAS1713599' is crossed with another basil plant to yield a hybrid, it can serve as either the maternal or paternal plant. For many crosses, the outcome is the same regardless of the assigned sex of the parental plants. Depending on the seed production characteristics relative to a second parent in a hybrid cross, it may be desired to use one of the parental plants as the male or female parent. Seed coat characteristics can be preferable in one plant. Pollen can be shed better by one plant. Therefore, a decision to use one parent plant as a male or female may be made based on any such characteristics as is well known to those of skill in the art.

J. Development of Basil Varieties

The development of new varieties using one or more starting varieties is well known in the art. In accordance with the invention, novel varieties may be created by crossing basil cultivar 'PAS1713599' followed by vegetative propagation of selected plants. In certain embodiments, novel varieties may be created by crossing basil cultivar 'PAS1713599' followed by multiple generations of breeding according to such well-known methods. New varieties may be created by crossing basil cultivar 'PAS1713599' with any second plant. In selecting such a second plant to cross for the purpose of developing novel varieties, it may be desired to choose those plants that either themselves exhibit one or more selected desirable characteristics or exhibit the desired characteristic(s) when in hybrid combination. Examples of potentially desired characteristics include foliage quality, shape and uniformity, maturity date, seed yield, seed germination rate, seedling vigor, pest and disease resistance, and adaptability for soil and climate conditions.

Once initial crosses have been made with basil cultivar 'PAS1713599', vegetative propagation or inbreeding takes place to produce new varieties. Inbreeding requires manipulation by human breeders. Even in the extremely unlikely event inbreeding rather than crossbreeding occurred in natural basil, achievement of complete inbreeding cannot be expected in nature due to well-known deleterious effects of homozygosity and the large number of generations the plant would have to breed in isolation. The reason for the breeder to create inbred plants is to have a known reservoir of genes whose gametic transmission is predictable.

The pedigree breeding method involves crossing two genotypes. Each genotype can have one or more desirable characteristics lacking in the other; or, each genotype can complement the other. If the two original parental genotypes do not provide all of the desired characteristics, other genotypes can be included in the breeding population. Superior plants that are the products of these crosses are selfed and selected in successive generations. Each succeeding generation becomes more homogeneous as a result of self-pollination and selection. Typically, this method of breeding involves five or more generations of selfing and selection: $S_1 \rightarrow S_2$; $S_2 \rightarrow S_3$; $S_3 \rightarrow S_4$; $S_4 \rightarrow S_5$, etc. After at least five generations, the inbred plant is considered genetically pure.

Uniform lines of new varieties may also be developed by way of double-haploids. This technique allows the creation of true breeding lines without the need for multiple generations of selfing and selection. In this manner true breeding lines can be produced in as little as one generation. Haploid induction systems have been developed for various plants to produce haploid tissues, plants, and seeds. The haploid induction system can produce haploid plants from any genotype by crossing with an inducer line. Inducer lines and methods for obtaining haploid plants are known in the art.

EXAMPLES

Example 1—Distinguishing Characteristics of Basil Cultivar 'PAS1713599'

The most distinguishing characteristics of basil cultivar 'PAS1713599' include late flowering, an upright habit, small leaves, and downy mildew resistance. For example, Tables 2 and 3 illustrates that plants of 'PAS1713599' have significantly smaller leaves and measured by leaf length and width than plants of PROSPERA 'PS5'. This trait is consistent across all trials conducted.

TABLE 2

Leaf length differences

| Trial | 'PAS1713599' Average Leaf Length (cm) | PROSPERA 'PS5' Average Leaf Length (cm) | Sample Size Each Variety | t Critical $\alpha = .05$ | t Statistic | P Value |
|---|---|---|---|---|---|---|
| Elburn IL | 5.9 +/− 0.3 | 10.5 +/− 0.7 | 15 | 2.0 | −23.4 | 6.3E−20 |
| Santa Paula CA | 5.8 +/− 0.5 | 8.2 +/− 0.7 | 15 | 2.0 | −11.1 | 9.1E−12 |

TABLE 3

Leaf width differences

| Trial | 'PAS1713599' Average Leaf Width (cm) | PROSPERA 'PS5' Average Leaf Width (cm) | Sample Size Each Variety | t Critical $\alpha = .05$ | t Statistic | P Value |
|---|---|---|---|---|---|---|
| Elburn IL | 3.6 +/− 0.3 | 5.8 +/− 0.4 | 15 | 2.0 | −19.4 | 9.1E−18 |
| Santa Paula CA | 3.2 +/− 0.2 | 4.5 +/− 0.4 | 15 | 2.0 | −13.0 | 2.3E−13 |

Resistance to basil downy mildew, caused by the pathogen *Peronospora belbahrii*, was evaluated at two locations, Santa Paula, California and Elburn, Illinois. Plants were grown in both the field and quart containers. Both the incidence and severity of basil downy mildew were rated on a 1 to 9 scale with an incidence rating of 1 being greater than 70% of all leaves and with symptoms and 9 all healthy leaves and a severity rating of 1 being 100% dead leaves and 9 all healthy leaves. Details of rating systems are shown below in Table 4 and the resistance ratings are shown in Table 5. In all trials, 'PAS1713599' was rated with the highest resistance to basil downy mildew that was comparable to highly resistance commercial comparisons.

TABLE 4

Basil Downy Mildew Resistance Rating Systems

| Scale | DM Incidence |
|---|---|
| 1 | >70% of all leaves with symptoms |
| 2 | 60 to 70% of all leaves with symptoms |

TABLE 4-continued

Basil Downy Mildew Resistance Rating Systems

| Scale | DM Incidence |
|---|---|
| 3 | 50 to 60% of all leaves with symptoms |
| 4 | 40 to 50% of all leaves with symptoms |
| 5 | 30 to 40% of all leaves with symptoms |
| 6 | 20 to 30% of all leaves with symptoms |
| 7 | 10 to 20% of all leaves with symptoms |
| 8 | <10% leaves with symptoms |
| 9 | Healthy |

| Scale | DM Severity |
|---|---|
| 1 | all dead material |
| 2 | much dead foliage |
| 3 | many heavy spores, yellow foliage and beginning of black dead foliage |
| 4 | many heavy spores and yellowing foliage increases |
| 5 | spores appear heavy, very large, little chlorosis |
| 6 | spores are observed heavy, very large, no chlorosis |
| 7 | spores are observed medium |

TABLE 4-continued

Basil Downy Mildew Resistance Rating Systems

| | |
|---|---|
| 8 | spores are observed light, very small |
| 9 | Healthy without symptoms |

In all trials. 'PAS1713599' was rated with the highest resistance to basil downy mildew that was comparable to highly resistance commercial comparisons.

TABLE 5

Basil Downy Mildew Resistance Ratings

| Cultivar | Trial | Average DM Incidence | Average DM Severity |
|---|---|---|---|
| 'PAS1713599' | Field IL | 9 | 9 |
| | Quart IL | 9 | 9 |
| | Field CA | 9 | 9 |
| | Quart CA | 9 | 9 |

TABLE 5-continued

Basil Downy Mildew Resistance Ratings

| Cultivar | Trial | Average DM Incidence | Average DM Severity |
|---|---|---|---|
| 'Dolce Fresca' | Field IL | 1 | 1 |
| | Quart IL | 3 | 5 |
| | Field CA | 1 | 2 |
| | Quart CA | 7 | 6 |
| PROSPERA 'CG1' | Field IL | 9 | 9 |
| | Quart IL | 9 | 9 |
| | Field CA | 9 | 9 |
| | Quart CA | 9 | 9 |
| PROSPERA 'PS5' | Field IL | 9 | 9 |
| | Quart IL | 9 | 9 |
| | Field CA | 9 | 9 |
| | Quart CA | 9 | 9 |

All of the compositions and methods disclosed and claimed herein can be made and executed without undue experimentation in light of the present disclosure. While the compositions and methods of this invention have been described in terms of the foregoing illustrative embodiments, it will be apparent to those of skill in the art that variations, changes, modifications, and alterations may be applied to the composition, methods, and in the steps or in the sequence of steps of the methods described herein, without departing from the true concept, spirit, and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope, and concept of the invention as defined by the appended claims.

The references cited herein, to the extent that they provide exemplary procedural or other details supplementary to those set forth herein, are specifically incorporated herein by reference.

What is claimed is:

1. A basil plant of cultivar 'PAS1713599', a representative sample of seed of the cultivar having been deposited under NCMA Accession No. 202602003.

2. A seed that produces the plant of claim 1.

3. A plant part of the plant of claim 1, wherein the plant part comprises a cell of the plant.

4. The plant part of claim 3, defined as a cutting, stem, leaf, axillary bud, flower, pollen, or ovule.

5. A basil plant having all of the physiological and morphological characteristics of the plant of claim 1.

6. A tissue culture of regenerable cells of the plant of claim 1.

7. A basil plant regenerated from the tissue culture of claim 6, wherein said plant has all of the physiological and morphological characteristics of basil cultivar 'PAS1713599'.

8. A method of vegetatively propagating the plant of claim 1, the method comprising the steps of:
  (a) collecting tissue capable of being propagated from the plant of claim 1; and
  (b) propagating a basil plant from the tissue.

9. A method of introducing a trait into a basil plant, the method comprising:
  (a) utilizing as a recurrent parent the plant of claim 1 by crossing the plant with a donor basil plant that comprises a trait to produce $F_1$ progeny;
  (b) selecting an $F_1$ progeny that comprises the trait;
  (c) backcrossing the selected $F_1$ progeny with a plant of the same basil cultivar used as the recurrent parent in step (a) to produce backcross progeny;
  (d) selecting a backcross progeny comprising the trait and the morphological and physiological characteristics of the recurrent parent basil cultivar used in step (a); and
  (e) repeating steps (c) and (d) three or more times to produce a selected fourth or higher backcross progeny.

10. A basil plant produced by the method of claim 9.

11. A method of producing a basil plant comprising an added trait, the method comprising introducing a transgene conferring the trait into the plant of claim 1.

12. A basil plant produced by the method of claim 11.

13. The plant of claim 1, further comprising a transgene.

14. The plant of claim 13, wherein the transgene confers a trait selected from the group consisting of herbicide tolerance, insect resistance, pest resistance, disease resistance, and environmental stress tolerance.

15. The plant of claim 1, further comprising a single locus conversion.

16. The plant of claim 15, wherein the single locus conversion confers a trait selected from the group consisting of herbicide tolerance, insect resistance, pest resistance, disease resistance, and environmental stress tolerance.

17. A method of plant breeding comprising applying plant breeding techniques to a plant according to claim 1.

18. The method of claim 17, defined as comprising producing a basil cultivar 'PAS1713599'-derived basil plant.

19. The method of claim 17, wherein said plant breeding techniques comprise recurrent selection, mass selection, hybridization, open-pollination, backcrossing, modified backcrossing, pedigree breeding, mutation breeding, or marker assisted selection.

20. The method of claim 17, further defined as comprising selecting a basil cultivar 'PAS1713599'-derived basil plant that comprises a late flowering trait, an upright habit, small leaves, or downy mildew resistance found in basil plant of cultivar 'PAS1713599'.

21. A method of producing a seed of a basil cultivar 'PAS1713599'-derived basil plant, the method comprising the steps of:
  (a) producing a basil cultivar 'PAS1713599'-derived basil plant from a seed produced by crossing a plant of claim 1 with itself or a second basil plant; and
  (b) crossing the basil cultivar 'PAS1713599'-derived basil plant with itself or a different basil plant to obtain a seed of a further basil cultivar 'PAS1713599'-derived basil plant.

22. The method of claim 21, the method further comprising repeating the producing and crossing steps of (a) and (b) using the seed from step (b) for producing a plant according to step (a) for at least one generation to produce a seed of an additional basil cultivar 'PAS1713599'-derived basil plant.

* * * * *